US006725865B2

(12) United States Patent
Chapman

(10) Patent No.: US 6,725,865 B2
(45) Date of Patent: Apr. 27, 2004

(54) SOFT CIRCULAR RESTRAINT APPARATUS AND METHOD

(75) Inventor: Bruce Chapman, Gardiner, NY (US)

(73) Assignee: Handle With Care, Inc, Gardiner, NY (US)

( * ) Notice: Subject to any disclaimer, the term of this patent is extended or adjusted under 35 U.S.C. 154(b) by 0 days.

(21) Appl. No.: 10/044,718

(22) Filed: Jan. 11, 2002

(65) Prior Publication Data

US 2002/0092531 A1 Jul. 18, 2002

Related U.S. Application Data

(60) Provisional application No. 60/261,699, filed on Jan. 16, 2001, and provisional application No. 60/327,670, filed on Oct. 6, 2001.

(51) Int. Cl.[7] .................................................. A61F 5/37

(52) U.S. Cl. ........................ 128/869; 128/876; 128/879

(58) Field of Search ................................ 128/846, 869, 128/870, 874, 875, 876; 2/312, 315, 316, 317, 318, 322, 338

(56) References Cited

U.S. PATENT DOCUMENTS 5,012,821 A * 5/1991 Tarver ........................ 128/876
5,309,926 A * 5/1994 Mayton ...................... 128/869
5,526,824 A * 6/1996 McAllister .................. 128/869
6,179,677 B1 * 1/2001 Dornier ...................... 441/113
6,279,799 B1 * 8/2001 Horton ....................... 284/275

* cited by examiner

*Primary Examiner*—Michael A. Brown
(74) *Attorney, Agent, or Firm*—Edward Etkin, Esq.

(57) ABSTRACT

An apparatus and method for restraining a person's limbs are disclosed. The inventive apparatus includes at least one cuff module for application to the person's limbs. An optional interconnect may be provided for each set of cuff modules. Each cuff module includes a flat flexible elongated body with two rigid loops positioned apart from each other on its upper surface, a resilient lining positioned along a portion of the lower surface of the cuff body, the resilient lining being optionally removable, a flat rigid element attached to one end of the cuff body, and a releasable attachment device positioned on portions of the top and bottom surfaces of the cuff body. When the cuff module is applied to a limb, the cuff body is positioned around the limb such that the resilient lining wraps around the limb, and the rigid element is threaded initially through one rigid loop and then through the other rigid loop and pulled so that the body is tightened around the limb, and portions of the top and the bottom surfaces, on which the releasable attachment device is disposed, come into releasable attachment with one another to releasably secure the cuff module around the limb such that the cuff module cannot be unwrapped without first removing the rigid element from the second loop and then disengaging the releasable attachment device. An optional elastic band may be positioned on the top surface of the body to store a portion of the cuff body folded upon itself at least once when the cuff module is in a storage position.

36 Claims, 5 Drawing Sheets

SOFT CIRCULAR RESTRAINT APPARATUS AND METHOD

REFERENCE TO PREVIOUSLY FILED APPLICATIONS

The present patent application claims priority from a previously filed commonly assigned U.S. Provisional Patent Application Ser. No.: 60/261,699, entitled "Soft Circular Restraint Apparatus and Method" filed on Jan. 16, 2001 and from a previously filed commonly assigned U.S. Provisional Patent application Ser. No.: 60/327,670, entitled "Soft Circular Restraint with Removable Lining Apparatus and Method" filed on Oct. 6, 2001.

BACKGROUND OF THE INVENTION

The present invention is directed to a soft mechanical restraint system that may be easily and quickly deployed by a first person on a subject being held in a restrained position by a second person.

There are many thousands of human service and law enforcement agencies and facilities that provide care and supervision to aggressive, suicidal, and emotionally disturbed persons (hereinafter commonly referred to as "EDPs"). The staff and officers working in these agencies regularly come into physical contact with the EDPs through the use of physical subduing or restraint holds when the EDP becomes aggressive. Although there are many types of well-known physical subduing holds, the safest and most advantageous physical subduing hold is a Primary Restraint Technique (PRT) described in greater detail in a commonly assigned U.S. Pat. No. 6,273,091 entitled "APPARATUS AND METHOD FOR SAFELY MAINTAINING A RESTRAINING HOLD ON A PERSON".

While restraint holds are useful for relatively short periods of time, often restraint of the EDP is necessary for an extended period. In such cases, the EDP must be restrained using some sort of a mechanical restraint system. Typically this involves placing wrist and ankle mechanical restraints on the EDP so that the EDP may be restrained for an extended period of time at the place of the restraint hold, or transported to another location while wearing the restraints. Most previously known restraint systems involve mechanical locks—for example, one popular restraint utilizes a mechanical spring-loaded lock that requires a special key to open. It takes at least 4–5 staff members to successfully apply such restraints at a speed of no lower than 2–3 minutes per restraint. During the application of these restraints, the EDP must be held down and poses a constant threat to the staff members until the restraining process is complete. Furthermore, removal of such restraints in emergency situations (i.e. in a medical emergency) takes a significant amount of time since a key must be located and used to open each restraint on each limb—this is especially problematic because without the key, which may not be immediately available in case of an emergency, the restraints cannot be removed at all. Finally, such complex restraint systems are expensive, heavy, and require extensive training to use properly.

Certain more recently developed restraints include mechanical locks based on a belt-like mechanism similar to a clothing belt with a buckle and a portion of the restraint having holes therein. Other similar restraints include a protruding metal member on one portion of the restraint and slots cut into the body of the restraint such that when the restraint is applied to the EDP, the portion with slots is pulled over the portion with the metal member until the restraint is tightened and the metal member is pushed through one of the slots. The end section of the slot portion may be further secured to the restraint. One of the main drawbacks with this arrangement is the fact that it is impossible to fit the restraint exactly to the hand or foot of the EDP since the restraint can only be tightened in increments equal to distance between the slots. As a result, it is possible that the restraint will be too loose (making it easier for the EDP to remove their limb from the restraint) or too tight (posing a danger of cutting off blood flow to the limb). Furthermore, a struggling unsupervised EDP may be able to loosen the restraint by pushing the slot portion of the restraint away from the metal member. Finally, all types of above restraints require special custom-made connectors to connect to one another or to stationary positions (i.e. a bed, etc.).

Thus, it would be desirable to provide an apparatus and method for quickly and easily applying mechanical restraints to a person being controlled through a restraining hold or who is otherwise immobile. It would furthermore be desirable to provide a mechanical restraint apparatus that is comfortable to the subject and that may be quickly and easily removed in case of an emergency. It would additionally be desirable to provide a mechanical restraint system that can provide a secure fit to limb of any size. It would further be desirable to provide a mechanical restraint system that can be attached to commonly available stationary connectors. It would also be desirable to provide a lightweight mechanical restraint system that is easy to transport and use, and that is inexpensive to manufacture.

SUMMARY OF THE INVENTION

The apparatus of the present invention and method of use thereof remedies the problems associated with applying mechanical restraints to violent and/or struggling EDPs (and with removing the restraints therefrom). In brief summary, the inventive soft circular restraints advantageously provide: (1) quick and easy application to the EDP without requiring mechanical locks or alignment of slots with metal members; (2) comfort to the EDP due to the soft constriction of the restraints; (3) quick and easy removal in case of an emergency; (4) a secure fit to any limb size as the inventive restraints are dynamically fitted exactly to the EDP limb size during application thereof; (5) easy attachment to commonly available stationary connectors, such as seat belt buckles; and (6) lightweight and simple construction, making the inventive restraints easy to transport and use and inexpensive to manufacture.

The inventive mechanical restraint apparatus consists of multiple cuff modules—two sized for arms and two sized for legs. Of course each cuff module may be utilized independently of one another. The arm cuff modules may be connected to one another by an interconnect, such as a piece of flexible but strong synthetic webbing (e.g. such as used in seat-belts) or a chain. Similarly, the leg cuff modules may also be interconnected in a similar manner. Optionally, each interconnect may be provided with a tensioning mechanism to control the interconnect length.

Each cuff module includes a flat flexible elongated body with two rigid loops positioned apart from each other on its upper surface, a resilient lining positioned along a portion of the lower surface of the body, the resilient lining being optionally removable, a flat rigid element attached to one end of the cuff body, and a releasable attachment device positioned on portions of the top and bottom surfaces of the cuff body. When the cuff module is applied to a limb, the cuff body is positioned around the limb such that the resilient lining wraps around the limb and the rigid element is threaded initially through one rigid loop and then through the other rigid loop and pulled, so that the cuff body is tightened around the limb, and portions of the top and the bottom surfaces, on which the releasable attachment device is disposed, come into releasable attachment with one another to releasably secure the cuff module around the limb, such that the cuff module cannot be unwrapped without first removing the rigid element from the second loop and then disengaging the releasable attachment device. An optional elastic band may be positioned on the top surface of the cuff body to store a portion of the cuff body folded upon itself at least once when the cuff module is in a storage position.

The inventive apparatus may be advantageously utilized once the EDP is restrained and placed into a controlled hold (or when the EDP is otherwise rendered immobile such as being asleep or unconscious). The cuff module is easily deployed from a storage position, by opening the cuff and pulling the rigid element which releases the folded portion of the cuff body from its folded position under the elastic band. Once the cuff module is placed around the EDP's wrist (or ankle), the rigid element is threaded through the first loop and then through the second loop in an intuitive circular motion. As the rigid element is pulled, the cuff module is tightened, and the releasable attachment device secures the cuff module in a closed position. The rigid element may then be attached to an optional external restraint device, such as a stationary bed connector or the like.

The inventive cuff module is easy to deploy because the staff member only has to pull on the rigid element to release the folded cuff body portion from its storage position, close the cuff module around the EDP's wrist (or ankle) and then just intuitively thread the rigid element through two loops in a circular motion around the cuff core—the releasable attachment device automatically secures the cuff module in the closed position. All together, the lightweight inventive cuff module can withstand approximately 10,000 pounds of force, all without any metal key elements.

Other objects and features of the present invention will become apparent from the following detailed description considered in conjunction with the accompanying drawings. It is to be understood, however, that the drawings are designed solely for purposes of illustration and not as a definition of the limits of the invention, for which reference should be made to the appended claims.

BRIEF DESCRIPTION OF THE DRAWINGS

In the drawings, wherein like reference characters denote corresponding or similar elements throughout the various figures.

DESCRIPTION OF THE PREFERRED EMBODIMENTS

Figures 1A, 1B, 1E:
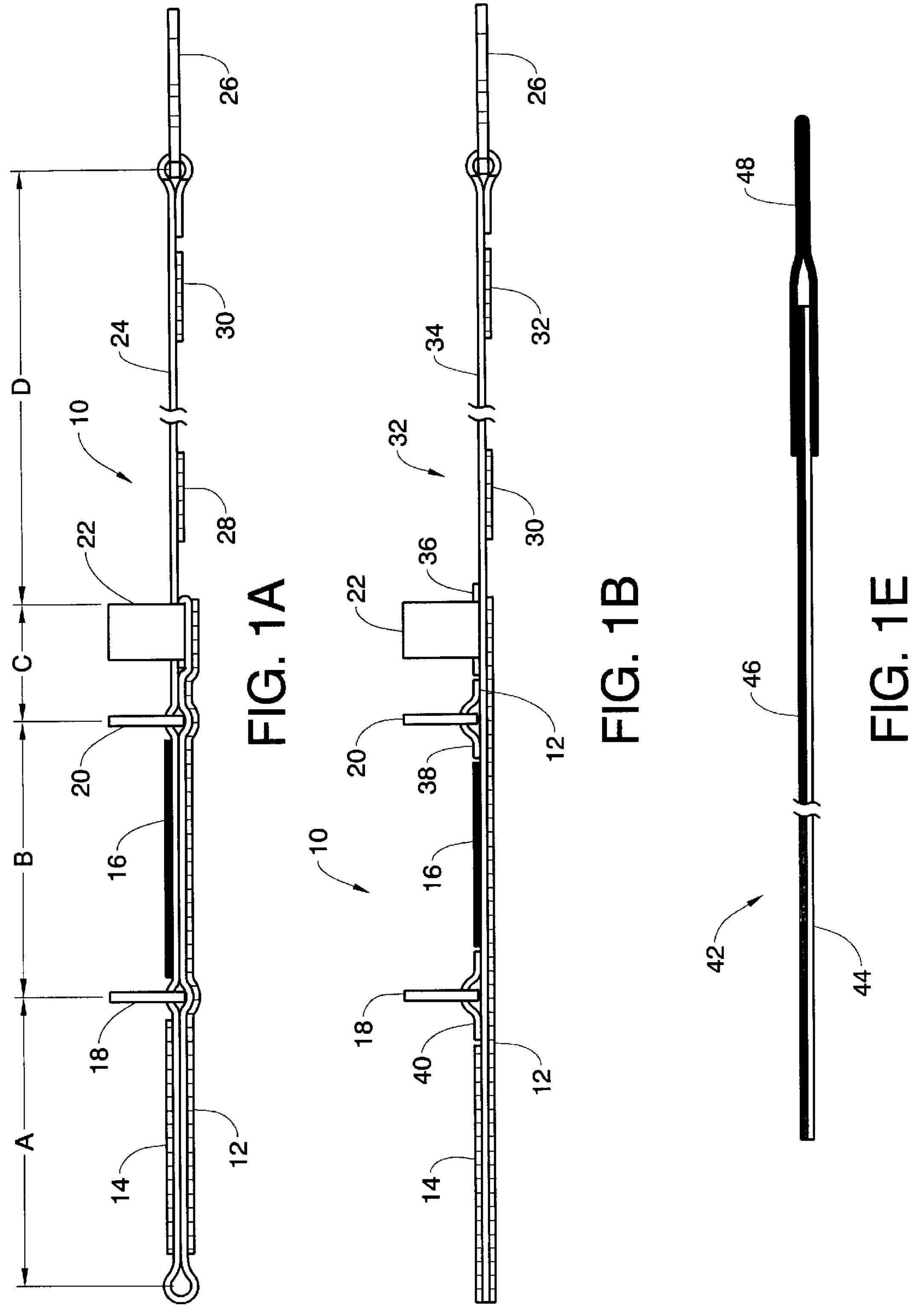
FIG. 1A shows a side view of a first embodiment of the circular restraint of the present invention in a open and extended position.
FIG. 1B shows a side view of a second embodiment of the circular restraint of the present invention in a open and extended position.
FIG. 1E shows a side view of an extended restraint liner for use with the circular restraint of FIG. 1A or 1B.

The present invention relates to an advantageous soft circular mechanical restraint apparatus and method that may be quickly and easily applied by a first person to a subject being held in a restraining hold by a second person, or to a subject who is otherwise immobilized (e.g. unconscious, sedated, asleep, etc.).

It should be understood that while the present invention refers to Emotionally Disturbed Persons (hereinafter "EDPs") and Staff Members, the inventive techniques and apparatus may be applied in virtually any situation where a subject is being restrained and application of mechanical restraints is warranted. Thus, the present invention is applicable in law enforcement, hospitals, mental health care facilities, drug and alcohol rehabilitation centers, etc.

Before application of any sort of mechanical restraints, it is important that control over a struggling EDP is established by placing the EDP into a restraining hold. The Primary Restraint Technique (hereinafter "PRT") is an advantageous modular single person restraint that is applied by an EDP care professional (hereinafter "staff member") to an EDP from behind. The maneuvers involved in implementing the PRT are described in greater detail in Primary Restraint Technique (PRT) described in greater detail in a commonly assigned U.S. Pat. No. 6,273,091 entitled "APPARATUS AND METHOD FOR SAFELY MAINTAINING A RESTRAINING HOLD ON A PERSON" which is hereby incorporated by reference in its entirety. It should be noted, however, that the restraint system of the present invention does not require use of the PRT—it may be advantageously be utilized in any situation where the EDP is physically restrained by one or more staff members or other individuals. Of course, if the EDP is not ambulatory (i.e. unconscious or asleep) it is not necessary to apply any restraint holds before application of the inventive restraints.

In summary, the inventive mechanical restraint apparatus comprises a cuff module for each of the person's limbs. Preferably, two cuff modules sized for wrists and two cuff modules sized for ankles are provided, although a single size module may be readily utilized for both wrists and ankles for EDPs of certain sizes. Thus, it should be noted that while the exemplary inventive cuff modules are shown in the drawings and described below as being applied to wrists, the inventive cuff modules may be readily applied to ankles, as ankle cuff modules are identical to the wrist modules in all respects except optionally being larger sized. Optionally, each set of writs and ankle cuff modules may be color-coded for easy identification. For example, the wrist cuff modules may be blue while the ankle cuff modules may be red.

Of course, in accordance with the present invention, less than four cuff modules may be utilized depending on circumstances, without departing from the spirit of the invention. For example, in some cases only the wrist cuff modules may be applied to the EDP. The inventive cuff modules may also be provided with optional interconnects that connect each set of cuff modules to one another. Thus, the wrist cuff modules may be supplied with wrist interconnects, and the ankle cuff modules may be supplied with ankle interconnects.

Furthermore, while the various embodiments of the inventive apparatus are described with references to particular hook and loop material strips positioned on various portions of the inventive cuff module, any loop and hook material strips may be interchanged between one another throughout the cuff module as long as the interchange is consistent overall, as a matter of design choice.

Referring now to FIG. 1A, a first embodiment of a cuff module 10 is shown. The cuff module 10 includes an elongated cuff body 24 composed of a strong flexible material such as nylon webbing (for example, the webbing used in seat belts and parachute straps) with a top surface and a bottom surface, a first end and a second end. A rigid element 26 is connected to the second end of the cuff body 24. The rigid element 26 is preferably composed of a hard material such as metal, hard plastic, or metal coated with a resilient material. The main purpose of the rigid element 26 is to allow the person applying the restraint to easily manipulate the second end of the cuff body 24. Optionally, the rigid element 26 may be configured as a connector that may be connected to an external stationary restraint device (as described below in connection with FIGS. 2C and 3) or to a cuff module interconnect (as described below in connection with FIGS. 4A and 4B). For example, the rigid element 26 may be a male seat-belt type connector.

A first rigid loop 18 is positioned perpendicular to the top surface of the cuff body 24, at a distance A away from the cuff body 24 first end. The rigid loop 18 is preferably generally rectangular and composed of a strong material such as metal, hard plastic, or metal coated with a resilient material. The opening in the rigid loop 18 is sized and configured to allow the rigid element 26 and a portion of the cuff body 24 to readily pass therethrough. Preferably, the rigid loop 18 has a limited range of pivoting motion about its lower portion by which it is attached to the cuff body 24, however, the rigid loop 18 may also be secured in a non-movable or very limited pivot position perpendicular to the cuff body 24. A second rigid loop 20 is positioned perpendicular to the top surface of the cuff body 24 a distance B away from the first rigid loop 18, between the rigid loop 18 and the second end of the cuff body 24. The rigid loop 20 is preferably identical to the rigid loop 18, being generally rectangular and composed of a strong material such as metal, hard plastic, or metal coated with a resilient material. The opening in the rigid loop 20 is sized and configured to allow the rigid element 26 and a several folds of the cuff body 24 to readily pass therethrough. Preferably, the rigid loop 20 has a limited range of pivoting motion about its lower portion by which it is attached to the cuff body 24, however, the rigid loop 20 may also be secured in a non-movable or very limited pivot position perpendicular to the cuff body 24.

A first hook material strip 14 (such as hook Velcro®) is positioned on the top surface of the cuff body 24 between the rigid loop 18 and the first end of the cuff body 24. Preferably, the hook material strip 14 fills a substantial portion of the area between the rigid loop 18 and the first end of the cuff body 24. However, the hook material strip 14 can be smaller than that area or be composed from multiple hook material strips (not shown). A first loop material strip 16 (such as loop Velcro®) is positioned on the top surface of the cuff body 24 between the rigid loop 18 and the rigid loop 20. Preferably, the loop material strip 16 fills a substantial portion of the area between the rigid loop 18 and the rigid loop 20. However, the loop material strip 16 can be smaller than that area, or be composed from multiple loop material strips (not shown). An optional elastic band 22 is positioned at a distance C away from the rigid loop 20, between the rigid loop 20 and the second end of the cuff body 24. The elastic band 22 may be cloth-coated rubber, or any other strong and resilient elastic material. The elastic band 22 is used when the cuff module 10 is in a storage position, as described below in connection with FIG. 2A.

An optional second hook material strip 12 (such as hook Velcro®) is positioned on the bottom surface of the cuff body 24, the length of the second hook material strip 12 preferably being approximately equal to sum of distances A and B (and optionally equal to the sum of distances A, B and C). However, the length of the second hook material strip 12 can be smaller than that the sum of Distances A and B or be composed from multiple loop material strips (not shown) disposed along an area between the first end of the cuff body 24 and the elastic band 22. The second hook material strip 12 is only necessary if the optional removable cuff liner 42 described below in connection with FIG. 1E is utilized. If the removable cuff liner 42 is not used, then the second hook material strip 12 is preferably replaced with a resilient (and optionally padded) material strip (not shown but having dimensions and position substantially similar to the second hook material strip 12) for contacting the EDP's limb and for providing relative comfort to the EDP. Optionally the resilient material strip may be coated with, or comprise, a non-skid layer such as "shark-skin" rubber to provide a better grip on the EDP's limb and to prevent the cuff module 10 from freely rotating about the limb.

A third hook material strip 30 (such as hook Velcro®) is positioned on the bottom surface of the cuff body 24, between the midpoint of a distance D and the second end of the cuff body 24. The third hook material strip 30 is preferably equal to or smaller in size to the loop material strip 16. The preferred position and size of the third hook material strip 30 is described below in connection with FIGS. 2A to 2C. An optional fourth hook material strip 28 (such as hook Velcro®) is positioned on the bottom surface of the cuff body 24, between the midpoint of a distance D and the elastic band 22. The preferred position and size of the fourth hook material strip 28 is described below in connection with FIGS. 2A to 2C. Optionally, either the entire area between the second hook strip 12 and the second end of the cuff body 24, or a large portion thereof, may be covered with either a single elongated hook material strip (not shown) or provided with additional hook material strips (in addition to the strips 28 and 30). The distance D is preferably greater than the sum of distances A, B and C.

In order to simplify fabrication of the cuff module 10 and to increase its strength, preferably, the cuff module body 24 is fabricated from a single long piece of webbing such that rigid loops 18 and 20, the elastic band 22 and the rigid element 26 are connected to the cuff body 24 by having one or more portions of the cuff body 24 folded upon itself and attached (e.g. sewn) to itself to encompass portions of the rigid loops 18 and 20, the elastic band 22 and the rigid element 26. One folding configuration of the cuff body 24 is shown in FIG. 1A by way of example only. Other configurations and schemes of folding portions of the cuff body 24 upon itself to attach at least some of rigid loops 18 and 20, the elastic band 22 and the rigid element 26 can be readily selected and implemented as a matter of design choice without departing from the spirit of the invention.

Referring now to FIG. 1B, a second embodiment of the cuff module 10 is shown as a cuff module 32. The cuff module 32 is functionally identical in all respects to the cuff module 10, except for the way the cuff module 32 is fabricated. The cuff module 32 comprises a cuff body 34 that is a simple elongated strip of a strong flexible material such as nylon webbing. However, instead of being attached by the cuff body 24 folded upon itself and attached to itself, the rigid loops 18 and 20 and the elastic band 22 are attached to the cuff body 36 by respective attachment devices 40, 38 and 36. The attachment devices 36, 38, and 40 may be small webbing strips sewn to the top surface of the cuff body 34 or other flexible attachment devices. In an alternate embodiment of the inventive cuff module (not shown) the cuff module 10 and cuff module 34 may be combined, where certain elements may be attached to a cuff body 24 or 34 by folding and attachment of the body to itself (as is done with the cuff module 10) while other elements may be attached to the cuff body 24 or 34 via one or more attachment devices such as attachment devices 36, 38, 40.

Figure 1C:
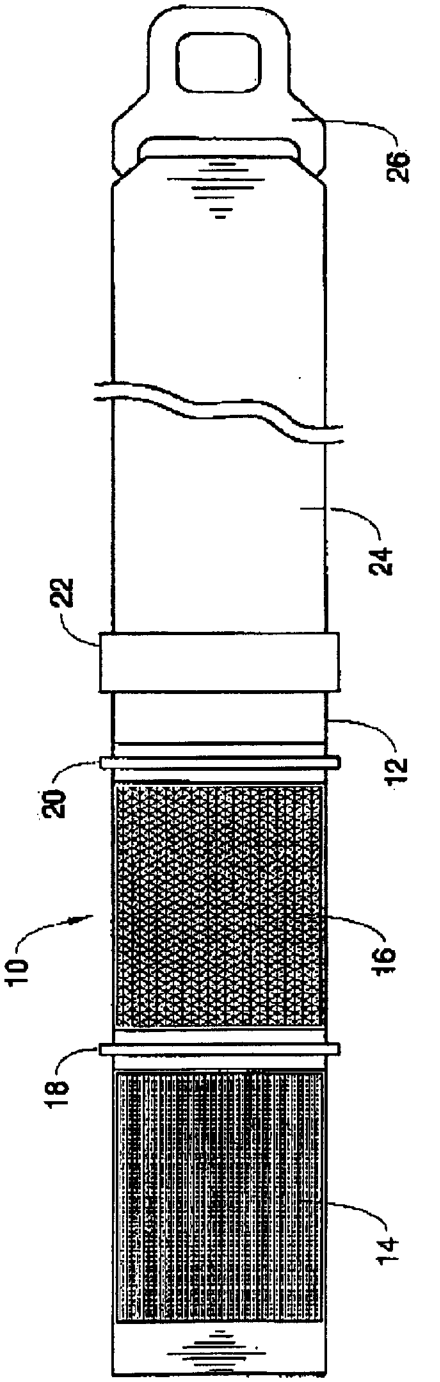
FIG. 1C shows a top view of the circular restraint of FIG. 1A or 1B in a open and extended position.
Figure 1D:
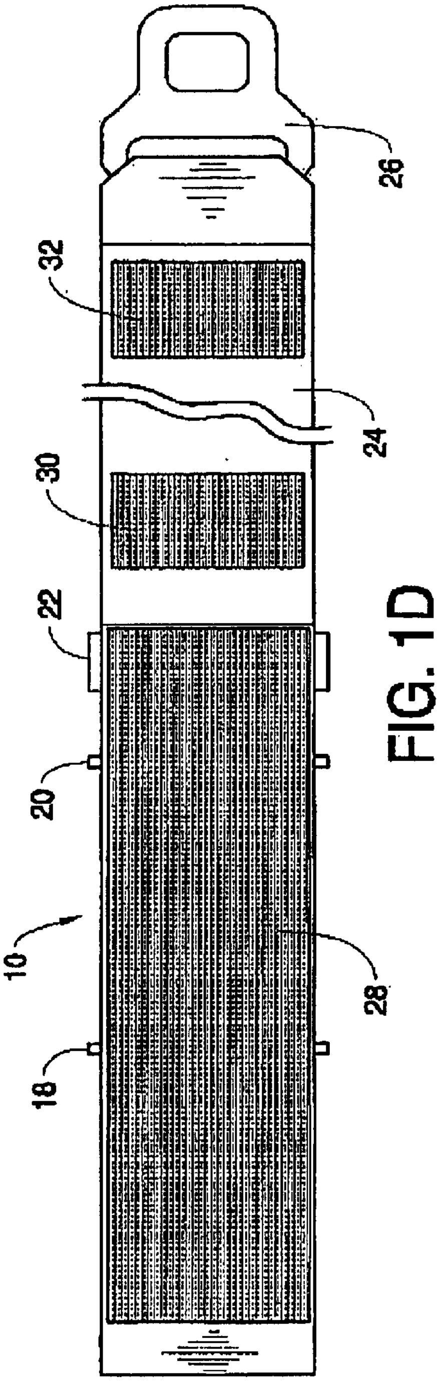
FIG. 1D shows a bottom view of the circular restraint of FIG. 1A or 1B in a open and extended position.

Referring now to FIG. 1C, a top view of the cuff module 10 is shown (the top view of the cuff module 34 of FIG. 1B looks identical). Referring now to FIG. 2B a bottom view of the cuff module 10 is shown (the bottom view of the cuff module 34 of FIG. 1B looks identical).

Referring now to FIG. 1E, the optional removable liner 42 is shown. The removable liner is disclosed in a previously filed commonly assigned co-pending U.S. Provisional Patent application entitled "Soft Circular Restraint with Removable Lining Apparatus and Method" from which the present application claims partial priority and which is hereby incorporated by reference in its entirety. The removable liner 42 comprises an upper layer 46 comprising a second loop material strip (such as loop Velcro®) preferably sized approximately equal to the second hook material strip 12. However, the upper layer 46 may be slightly smaller or larger than the second hook material strip 12 as a matter of design choice. The removable liner 42 also comprises a lower layer 44 of substantially the same size as the upper layer 46. The lower layer 44 is preferably a flexible resilient (and optionally padded) material strip for contacting the EDP's limb and for providing relative comfort to the EDP. Optionally, the lower layer 44 may be coated with, or comprise, a non-skid layer such as "shark-skin" rubber to provide a better grip on the EDP's limb and to prevent the cuff module 10 from freely rotating about the limb. Optionally, the lower layer 44 may be composed of an absorbent disposable material such as cotton and advantageously disposed after use, thus keeping the cuff module 10 clean and sterile.

The removable liner 42 also comprises a tab 48 for facilitating removal of the removable liner 42 from the cuff module 10. Preferably, the tab 48 is positioned over one of the ends of the removable liner 42 and extending beyond the upper and lower layers 46, 44 and composed of loop material (such as loop Velcro®). Optionally, the tab 48 may be composed of any other flexible material.

The removable liner 42 is removably attached to the second hook material strip 12 and positioned such that the end of the upper and lower layers 46, 44 having the tab 48 attached thereto is aligned with an area under the elastic band 22, and the tab 48 extends beyond the underside of the elastic band 22 toward the second end of the cuff body 24.

While the above elements 12, 14, 16, 28, 30, 42 and 48 are described with reference to either hook or loop material, it should be understood to one skilled in the art that any other flexible releasable attachment devices can be readily substituted for the hook and loop material without departing from the spirit of the invention. For example, two or more of the elements 12, 14, 16, 28, 30, 42 and 48 may be replaced with releasable glue strips or the like. This arrangement may be particularly advantageous if the removable liner 42 is configured as a disposable liner.

Figure 2A:
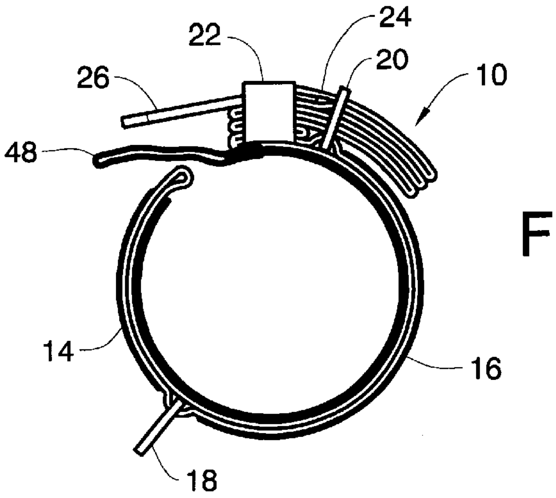
FIG. 2A shows a side view of the circular restraint of FIG. 1A in a storage position in preparation for application to a limb.
Figure 2B:
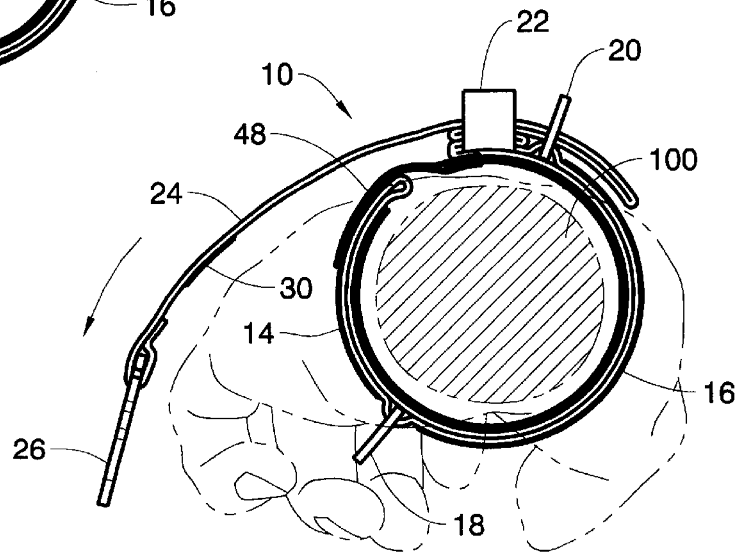
FIG. 2B shows a side view of circular restraint of FIG. 1A in an intermediate step of application to a limb.
Figure 2C:
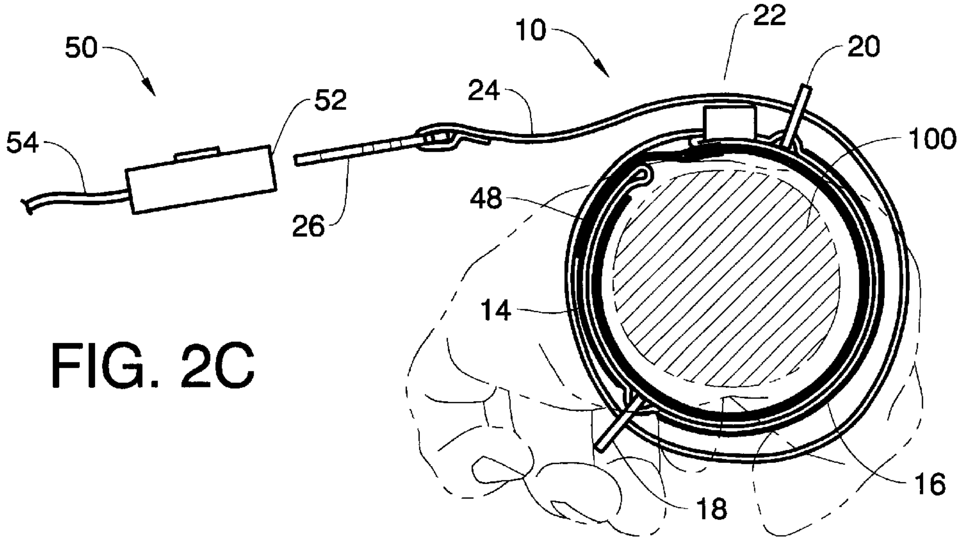
FIG. 2C shows a side view of circular restraint of FIG. 1A fully applied to a limb and a side view of an optional external restraint connector.
Figure 3:
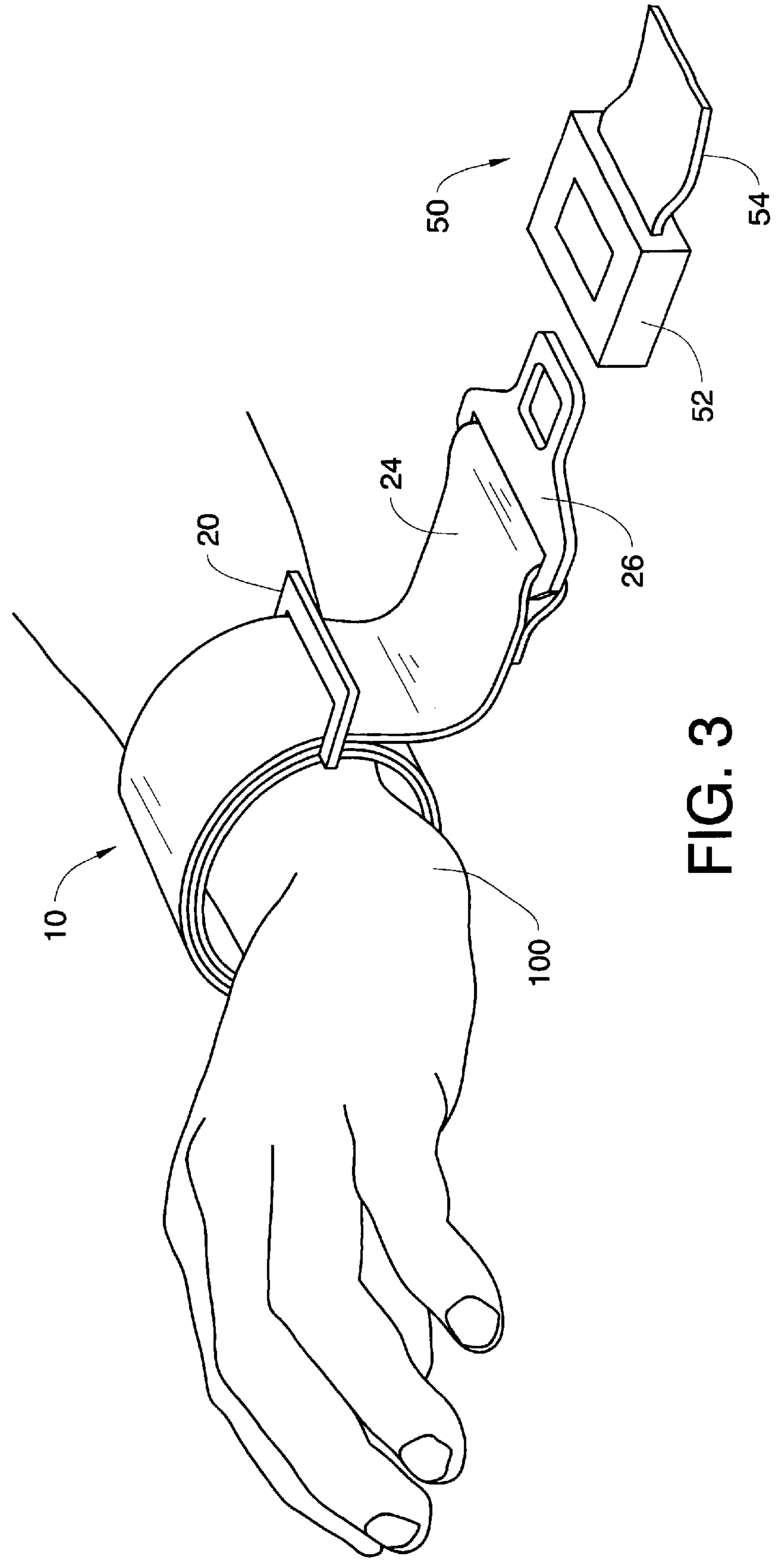
FIG. 3 shows a simplified top isometric view of circular restraint of FIG. 1A or 1B fully applied to a limb, and a top isometric view of an optional external restraint connector.

Referring now to FIGS. 2A to 2C, the operation of the cuff module 10 is shown as an exemplary application of the cuff module 10 to a wrist 100. In FIG. 2A the cuff module 10 is shown in a storage position where a portion of the cuff body 24 is folded upon itself and stowed under the elastic band 22 (and optionally retained by the rigid loop 20). Optionally, the rigid element 26 may also be stowed under the elastic band 22 but pointed away from the rigid loop 20. Referring now to FIG. 2B, the cuff module 10 is applied to the wrist 100 by first wrapping the cuff body 24 around the wrist 100 as tightly as possible, such that the resilient liner lower surface 44 is in contact therewith, and such that the tab 48 is releasably attached to a portion of the first hook material strip 14, thus at least temporarily securing the cuff module 10 around the wrist 100. Then, the rigid element 26 is pulled away from the elastic band 22 causing the folded portion of the cuff body 24 to unfold. Referring now to FIG. 2C, the rigid element 26 is then first threaded through the loop 18 and then threaded through the loop 20 in an intuitive circular motion. As the rigid element 26 is tightly pulled, the third hook material strip 30 forms a releasable attachment connection with the first loop material strip 16. Thus, the third hook material strip 30 should be sized, configured, and positioned along the bottom surface of the cuff body 24 in such a manner as to achieve contact with the first loop material strip 16 when the cuff module 10 is closed. Similarly, if the fourth hook material strip 28 is used, it forms a releasable attachment connection with the tab 48. Thus, the fourth hook material strip 28 should be sized, configured, and positioned along the bottom surface of the cuff body 24 in such a manner as to achieve contact with the tab 48 when the cuff module 10 is closed. If the rigid element 26 is configured as a connector, then it may be releasably attached to an external stationary restraint 50 having a connector 52 for releasably connecting to the rigid element 26, and a body 54. Referring to FIG. 3, an isometric top view of the cuff module 10 applied to the wrist 100 is shown.

Once various above-described hook and loop material strips are attached to one another, they can only be pulled apart by applying a force substantially perpendicular thereto. As a result, due to the circular nature of the cuff module 10 and the fact that a portion of the cuff body 10 is treaded through and secured by the rigid loops 18 and 20, it is impossible for the EDP to open the restraint on their own.

Advantageously, once the EDP is restrained and placed into a controlled hold (or when the EDP is otherwise disabled such as during sleep), the cuff module 10 may be easily deployed from the storage position and applied to the EDP by one person. The cuff module 10 is easy to deploy because the staff member only has to pull on the rigid element 26 to release the folded cuff body 24 portion from its storage position, close the cuff module 10 around the EDP's wrist (or ankle), and then just intuitively thread a portion of the cuff body 24 through two rigid loops 18, 20 in a circular motion—the hook and loop strips on the cuff body 24 top and bottom surfaces automatically secure themselves to one another. All together, the lightweight inventive cuff module 10 can withstand approximately 10,000 pounds of force, all without any metal key elements.

It takes less than 25 seconds for a single person to deploy the inventive cuff module 10 from a storage position to the deployed restraint position. Because all elements of the inventive systems are flexible and soft, the EDP will not hurt themselves or experience significant discomfort by struggling against the restraints. Most importantly, the inventive cuff module 10 may be removed in one second in an emergency situation without need for a special key. Moreover, the cuff module 10 of the present invention is easy and intuitive to use and inexpensive to manufacture.

Figures 4A, 4B:
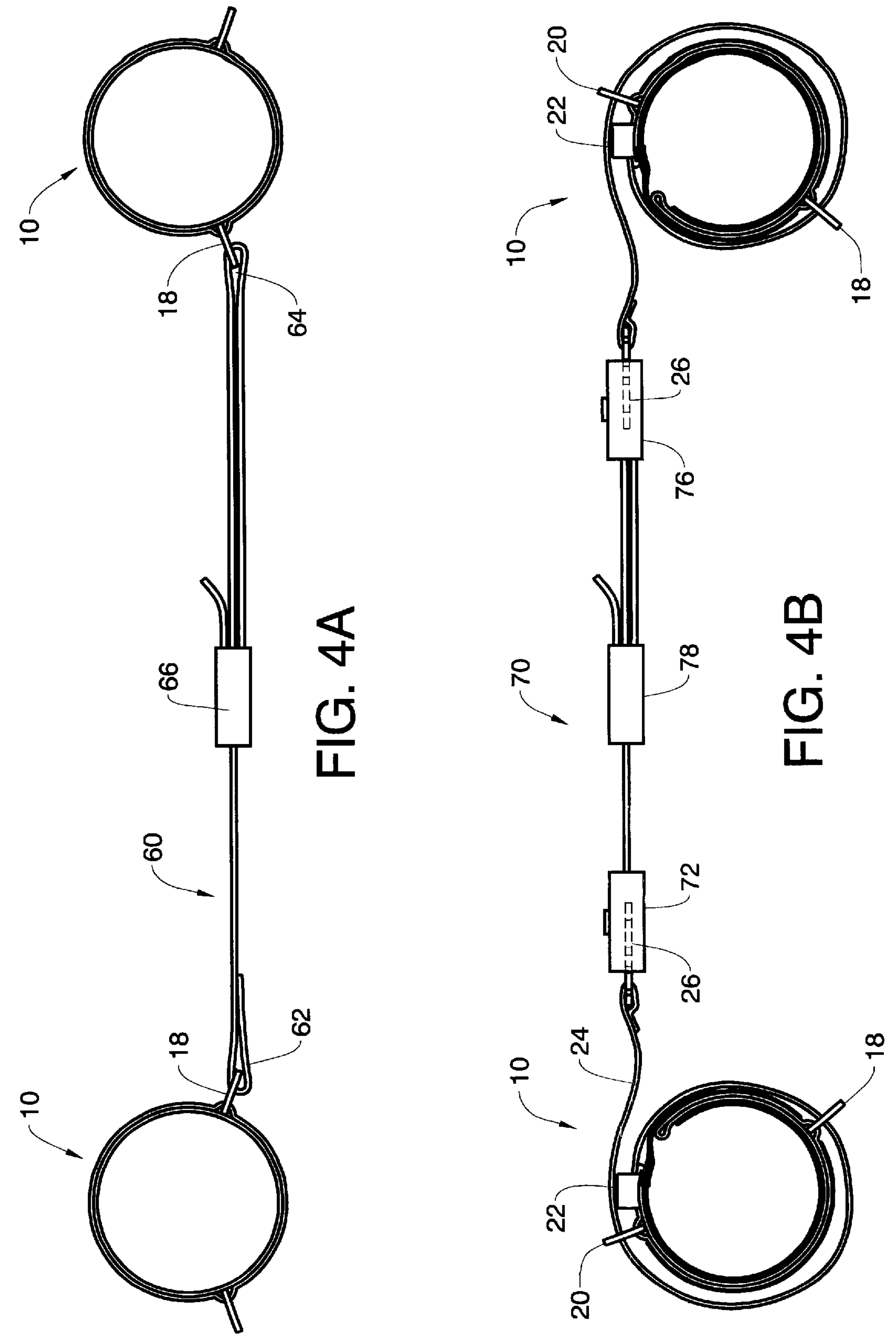
FIG. 4A shows a simplified side view of two sets of circular restraints of FIG. 1A or 1B, with a first embodiment of an optional restraint interconnect.
FIG. 4B shows a simplified side view of two sets of circular restraints of FIG. 1A or 1B, with a second embodiment of an optional restraint interconnect.

Referring now to FIG. 4A, a first embodiment of an optional cuff interconnect 60 is shown. The interconnect 60 may be composed of a flexible and strong material (such as nylon webbing) and is attached to the loop 18 of a first cuff module 10 via a connector 62 (which may be a webbing loop), and is also attached to the loop 18 of another cuff module 10 via a connector 64 (which may also be a webbing loop). The interconnect 60 may be of a predetermined length, or may be optionally supplied with a tensioning device 66 for adjusting the length of the interconnect 60, and thus the distance between the two cuff modules 10.

Referring now to FIG. 4A a second embodiment of an optional cuff interconnect 70 is shown. The interconnect 70 may be utilized with cuff modules 10 when the rigid element 26 is configured as a connector. The interconnect 70 may be composed of a flexible and strong material (such as nylon webbing), and is provided with a first releasable connector 72 at one end, and a second releasable connector 76 at the other end. The releasable connectors 72, 76 are preferably configured to releasably attach to the rigid elements 26 from each cuff module 10. For example, if the rigid element 26 is configured as a male seat belt connector, then the releasable connectors 72, 76 may be configured as female seat belt connectors. Once the cuff modules 10 are applied to each limb, the respective rigid elements 26 from each cuff module 10 may be readily attached to the corresponding releasable connectors 72, 76. The interconnect 70 may be of a predetermined length, or may be optionally supplied with a tensioning device 78 for adjusting the length of the interconnect 70, and thus the distance between the two cuff modules 10.

Thus, while there have shown and described and pointed out fundamental novel features of the invention as applied to preferred embodiments thereof, it will be understood that various omissions and substitutions and changes in the form and details of the devices and methods illustrated, and in their operation, may be made by those skilled in the art without departing from the spirit of the invention. For example, it is expressly intended that all combinations of those elements and/or method steps which perform substantially the same function in substantially the same way to achieve the same results are within the scope of the invention.

I claim:

1. A restraint apparatus for restraining a person, comprising:

a cuff module for application to the person's limb, said cuff module comprising:

a flat flexible elongated body of a predefined width, having a first end, a second end, a top surface and a bottom surface;

a first rigid loop positioned on said top surface of said body and perpendicular thereto, between said first end of said body and said second end of said body, wherein said first loop width is at least equal to said predefined width of said body; a second rigid loop positioned on said top surface of said body and perpendicular thereto, between said first loop and said second end of said body, wherein said first loop width is at least equal to said predefined width of said body;

a resilient lining of a predetermined length, configured to match said first width, positioned on said bottom surface and extending from a position proximal to said first end of said body toward said second end of said body;

a flat rigid element attached to said second end of said body; and first releasable attachment means, positioned on portions of said top and said bottom surface, for releasably attaching said portions of said top and said bottom surfaces to one another after application of said cuff module to a limb, wherein when said cuff module is applied to the limb, said body is positioned around the limb such that said resilient lining wraps around the limb, end said rigid element is threaded initially through said first rigid loop and then through said second rigid loop and pulled so that said body is tightened around the limb, and said portions of said top and said bottom surfaces are in contact with one another, and wherein said first releasable attachment means is engaged to releasably secure said cuff module around the limb such that said cuff module cannot be unwrapped without first removing said rigid element from said second rigid loop and then disengaging said first releasable attachment means.

2. The restraint apparatus of claim 1, further comprising: an elastic loop positioned on said top surface of said body between said second rigid loop and said second end of said body and proximal to said second rigid loop, said elastic loop being sized and configured to releasably retain a section of said body folded upon itself, wherein:

when said cuff module is in a storage configuration, said section of said body extending from said elastic loop to said second end is folded upon itself at least once and inserted through said elastic loop, such that said folded section is releasably retained by said elastic loop and said rigid element is pointed away from said first end of said body, and when said cuff module is prepared for application to the limb, said rigid element is pulled away from said first end, thereby releasing said folded section from said elastic loop and extending said section of said body.

3. The restraint apparatus of claim 2, wherein a portion of said folded body section is inserted through, and retained by, said second rigid loop.

4. The restraint apparatus of claim 1, wherein said rigid element is composed of at least one material selected from a group of: metal, hardened plastic, and metal coated with a resilient material.

5. The restraint apparatus of claim 1, wherein each of said first and said second rigid loops are composed of at least one material selected from a group of: metal, hardened plastic, and metal coated with a resilient material.

6. The restraint apparatus of claim 1, further comprising:

first attachment means for attaching said first rigid loop to said top surface of said body, and for allowing said first rigid loop a limited pivot range about an axis defined by said first rigid loop lower portion; and second attachment means for attaching said second rigid loop to said top surface of said body, and for allowing said second rigid loop a limited pivot range about an axis defined by said second rigid loop lower portion.

7. The restraint apparatus of claim 1, wherein said first and said second attachment means comprise an additional section of the body continuing from said first end, said additional section being folded over and secured to a length of one of said top and said bottom surfaces such that said lower portions of first and said second rigid loops are pivotably secured between one of said top and bottom surfaces and said additional section.

8. The restraint apparatus of claim 1, wherein said rigid element comprises a connector configured for connection to an additional restraint module.

9. The restraint apparatus of claim 8, wherein said rigid element comprises a male seat-belt type connector, and wherein said additional restraint module comprises a female seat-belt type connector.

10. The restraint apparatus of claim 1, wherein said resilient lining comprises an upper portion and a lower portion, wherein said upper portion is attached to said bottom surface of said body, and said lower portion is in contact with the limb when said cuff module is applied thereto, and wherein said lower portion is composed of a non-skid material to prevent said cuff module from freely rotating around the limb.

11. The restraint apparatus of claim 10, further comprising second releasable attachment means, positioned between said bottom surface of said body and said upper portion of said resilient lining, for releasably attaching said resilient lining to said body.

12. The restraint apparatus of claim 11, wherein said resilient lining further comprises a flexible tab positioned on one of its ends for facilitating removal of said resilient liner from said body.

13. The restraint apparatus of claim 11, wherein said second releasable attachment means comprises: one of hook or loop attachment material positioned on said bottom surface of said body, and the other of said hook or loop attachment material positioned along said upper portion of said resilient lining.

14. The restraint apparatus of claim 13, wherein said tab is composed of the same attachment material as positioned along said upper portion of said resilient lining.

15. The restraint apparatus of claim 14, further comprising: a first attachment material element of the same composition as the particular attachment material positioned on said bottom surface of said body, said first attachment material element being positioned between said first end and said first rigid loop, wherein when the restraint is applied to the limb and the resilient liner is wrapped around the limb, said tab is releasably attached to said first attachment material element so as to improve the resistance of said cuff module to undesirable release.

16. The restraint apparatus of claim 13, wherein said lower portion of said resilient lining comprises an absorbent non-skid disposable material.

17. The restraint apparatus of claim 1, wherein said body is composed from nylon webbing.

18. The restraint apparatus of claim 1, wherein said first releasable attachment means comprises:

a second attachment element comprising one of hook or loop attachment material, positioned on said top surface between said first and second rigid loops; and at least one additional attachment element comprising the other of hook or loop attachment material, positioned on said bottom surface between said second rigid loop and said second end of said body, wherein when said cuff module is applied to the limb and said rigid element is threaded through said first and said second rigid loops and said cuff module is tightened around the limb, said second and said at least one additional attachment elements are releasably attached to each other to releasably secure said cuff module around the limb, such that said cuff module cannot be unwrapped without first disengaging said second attachment element from said at least one additional attachment element.

19. The restraint apparatus of claim 1, wherein said cuff module is sized for application to the person's wrist.

20. The restraint apparatus of claim 19, wherein said cuff module is of a first color.

21. The restraint apparatus of claim 1, wherein said cuff module is sized for application to the person's ankle.

22. The restraint apparatus of claim 21, wherein said cuff module is of a second color.

23. The restraint apparatus of claim 1, further comprising a second cuff module, identical to said cuff module, applied to another one of the person's limbs.

24. The restraint apparatus of claim 23, further comprising interconnect means for connecting said cuff module to said second cuff module.

25. The restraint apparatus of claim 24, wherein said interconnect means comprises an elongated flexible connector having a first pan attached to said cuff module and a second part attached to said second cuff module.

26. The restraint apparatus of claim 25, wherein said first part of said flexible connector is attached to said first rigid loop of said cuff module and said second part of said flexible connector is attached to a corresponding first rigid loop of said second cuff module.

27. The restraint apparatus of claim 25, wherein said flexible connector is a chain.

28. The restraint apparatus of claim 25, wherein said flexible connector is a length of flexible webbing.

29. The restraint apparatus of claim 28, wherein said flexible connector further comprises: a first tensioning device to control the length of said flexible connector.

30. The restraint apparatus of claim 25, wherein said flexible connector comprises: a first releasable connector attached to said first part, that releasably attaches to said rigid element of said cuff module and a second releasable connector attached to said second part, that releasably attaches to a corresponding rigid element of said second cuff module.

31. The restraint apparatus of claim 30, wherein said flexible connector further comprises a second tensioning device to control the length of said flexible connector.

32. The restraint apparatus of claim 1, wherein said first and said second rigid loops are of different colors.

33. A method for restraining a person by applying restraints to at least one limb of a person, comprising the steps of:

(a) providing a cuff module comprising:

a flat flexible elongated body of a predefined width, having a first end, a second end, a top surface and a bottom surface;

a first rigid loop positioned on said top surface of said body and perpendicular thereto, between said first end of said body and said second end of said body, wherein said first loop width is at least equal to said predefined width of said body;

a second rigid loop positioned on said top surface of said body and perpendicular thereto, between said first loop and said second end of said body, wherein said first loop width is at least equal to said predefined width of said body;

a resilient lining of a predetermined length, configured to match said first width, positioned on said bottom surface and extending from a position proximal to said first end of said body toward said second end of said body; and a flat rigid element attached to said second end of said body;

(b) positioning said body around the limb such that said resilient lining wraps around the limb;

(c) threading said rigid element through said first rigid loop;

(d) threading said rigid element through said second rigid loop;

(e) pulling said rigid element so that said body is tightened around the limb; and (f) releasably securing said cuff module around the limb by releasably attaching portions of said top and said bottom surfaces of said body via a releasable attachment device as said body is tightened, such that said cuff module cannot be unwrapped without first disengaging said releasable attachment device.

34. The method of claim 33, further comprising the steps of:

(g) providing at least one additional cuff module far restraining at least one other limb; and (h) repeating said steps (a) through (e) for each of said at least one additional cuff module to secure at least one other limb of the person.

35. The method of claim 34, further comprising the step of:

(i) providing an interconnect device to connect said cuff module and one of said at least one additional cuff module to one another.

36. The method of claim 35, further comprising the step of:

(j) selecting a desirable the length of said interconnect device via a tensioning device positioned thereon.

* * * * *